United States Patent [19]

Nakamura et al.

[11] Patent Number: 4,623,394
[45] Date of Patent: Nov. 18, 1986

[54] GRADUALLY DISINTEGRABLE MOLDED ARTICLE

[75] Inventors: Satoshi Nakamura; Hiromi Hijiya; Toshio Miyake, all of Okayama, Japan

[73] Assignee: Kabushiki Kaisha Hayashibara Seibutsu Kagaku Kenkyujo, Okayama, Japan

[21] Appl. No.: 719,434

[22] Filed: Apr. 3, 1985

[30] Foreign Application Priority Data

Apr. 14, 1984 [JP] Japan .................................. 59-75576

[51] Int. Cl.$^4$ ............................................. C08L 5/00
[52] U.S. Cl. ................................... 106/122; 106/205; 106/208; 106/209
[58] Field of Search ............... 106/205, 208, 209, 122; 514/776

[56] References Cited

U.S. PATENT DOCUMENTS

| | | | |
|---|---|---|---|
| 2,949,397 | 8/1960 | Werner | 106/209 |
| 3,784,390 | 1/1974 | Hijiya et al. | 106/213 |
| 3,871,892 | 3/1975 | Hijiya et al. | 106/213 |
| 3,873,333 | 3/1975 | Hijiya et al. | 106/204 |
| 3,932,192 | 1/1976 | Nakashio et al. | 106/213 |
| 3,997,703 | 12/1976 | Nakashio et al. | 264/186 |
| 4,257,816 | 3/1981 | Yin et al. | 106/205 |

FOREIGN PATENT DOCUMENTS 1374199 11/1974 United Kingdom .
1533301 11/1978 United Kingdom .
1559644 1/1980 United Kingdom .

Primary Examiner—Theodore Morris
Attorney, Agent, or Firm—Browdy and Neimark

[57] ABSTRACT

A novel molded article exhibiting a gradual disintegration effect is prepared with pullulan. The effect is imparted by incorporating heteromannan into a pullulan molded article in an amount not exceeding the weight of the pullulan used. Galactomannans (e.g. guar gum, tara gum, and locust bean gum) and glucomannans (e.g. konjak mannan) are feasible as the heteromannan. The molded article is advantageously usable for industrial materials, pharmaceuticals, consumers' products, etc.

7 Claims, 2 Drawing Figures

GRADUALLY DISINTEGRABLE MOLDED ARTICLE

FIELD OF THE INVENTION

The present invention relates to a molded article which exhibits a controlled disintegrability under hydrous conditions.

DEFINITIONS

The term "molded article(s)" used herein includes various two- or three-dimensional molded articles prepared with pullulan; e.g. granule, fiber, filament, rod, gauze, cloth, film, sheet, paper, coating membrane, tube, capsule, tablet, sponge, laminated article, etc.

The percentages used herein are indicated by weight unless specified otherwise.

The "part(s)" used herein is indicated by weight.

BACKGROUND OF THE INVENTION

Pullulan, a viscous glucan, is produced and commercialized by culturing a microorganism of species *Aureobasidium pullulans* on a nutrient culture medium containing saccharide(s), e.g. monosaccharide, lower saccharide, etc., under aerobic conditions. Since pullulan has characteristic properties such as high moldability to form self-supporting membranes, water-solubility, edibility, transparency, oil-resistance, gas-barrier property, gloss and adhesion, is widely used to prepare various molded articles, e.g. granule, rod, film, sheet, tablet, etc.

As in the case of some pharmaceuticals, molded articles having a controlled dissolution/disintegration rate under hydrous conditions are in great demand because of the needs, e.g., to retain a medical efficacy for a prescribed period. Conventional molded articles have characteristic high-solubility and high-disintegrability in water. These natures, however, result in an excessive dissolution/disintegration rate as found in the conventional molded articles, and render the production of gradually disintegrable molded articles very difficult.

DESCRIPTION OF THE PREFERRED EMBODIMENTS

Figure 1:
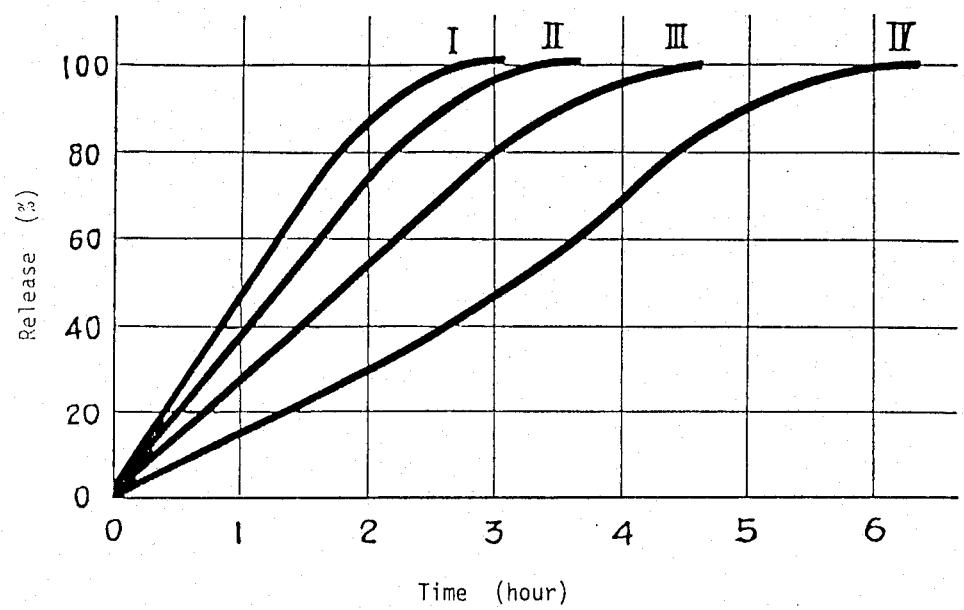
FIG. 1 graphically shows exemplary results of disintegration tests on several tablets prepared with a powder mixture of pullulan and a polysaccharide, wherein Curve I shows the disintegration feature of a tablet containing pullulan along with either gum arabic, pectin, carrageenan or karaya gum; Curve II, that of a tablet containing pullulan along with either dextran, elsinan, gum tragacanth or xanthan gum, Curve III, that of a tablet containing pullulan along with either guar gum or tara gum; Curve IV, that of a tablet containing pullulan along with either locust bean gum or konjak mannan. The control tablet prepared solely with pullulan disintegrates in accordance with Curve II.

To establish a molded article which will gradually disintegrate under hydrous conditions, and its production, we investigated various molded articles wherein one or more additional polysaccharides are used. We found that a molded article containing heteromannan meets the objects of the present invention. More particularly, we found that a molded article having an appropriate disintegrability can be obtained without loss of the high moldability attained with pullulan by incorporation of heteromannan. This is the present invention.

To obtain such molded article, conventional molding procedures, e.g., compression molding, transfer molding, laminating, injection molding, extrusion molding, blow molding, calendering, vacuum forming, coating, etc., are feasible. In order to prepare a molded article containing heteromannan, pullulan with a molecular weight in the range of 10,000–5,000,000 daltons is admixed with heteromannan in the course of manufacturing the molded article by a suitable procedure, e.g. mixing, kneading, applying, coating, spraying, soaking, permeating, injecting, etc., to give a powder, suspension or solution having highest possible homogeneity, preferably a solution mixture containing pullulan and heteromannan, or other homogenous mixture thereof, e.g. concentrate, alcohol precipitate, dry mixture solid, etc.

The heteromannans usable in the present invention include galactomannans such as guar gum, tara gum and locust bean gum, and glucomannans such as konjak mannan. The amount of heteromannan is, by weight on the basis of dry solids, less than that of the pullulan used, preferably, within the range of 1–80% of the pullulan. The molecular weight of heteromannan generally falls within the range of 50,000–10,000,000 daltons.

We parallelly investigated methods for detection of heteromannan. We found that heteromannan is easily gelatinized when 5 ml of about 0.5% aqueous heteromannan solution is placed in a test tube, and then admixed with several drops of about 4 w/v % aqueous borax solution. It was also found that polysaccharides, such as pullulan, gum arabic, dextran, elsinan, carrageenan, gum karaya, pectin, gum tragacanth and xanthan gum, do not present such gelatinization. Thus, we confirmed that this is usable as a convenient method for detecting heteromannan.

One or more substances, e.g. plasticizer, filler, vehicle, foaming agent, flame retarder, mold release, antibacterial agent, coloring agent, flavor, nutriments, tobacco, bioactive substance, pharmacuetical and tasting agent, can be incorporated into the molded article, so far as pullulan is present in the molded article in an amount at least 5%, preferably 10% or higher, and so far as the favorable natures of pullulan are elicited in the product.

The uses of the molded article produced according to the invention are not restricted to particulars. It is usable in various industries, e.g. agriculture, forestry, fisheries, stock raising and mining, as well as for consumer's products.

Now several natures of a film product will be given as an example to explain several features of the molded article according to the present invention.

(1) The film in accordance with the present invention is much more resistant to moisture and water, and, therefore, much more easily handleable than a film product prepared solely with pullulan. When the film is incorporated with a drug, the drug is gradually released to exhibit its efficacy as the disintegration of the film proceeds under hydrous conditions. The disintegrability of the film can be controlled by adjusting the ratio of heteromannan to pullulan.

(2) The film is superior in tensile strength, flexibility and stretchability to a film product prepared solely with pullulan.

(3) The film is colorless, transparent, tasteless, odorless, non-toxic and edible. It is usable as a coating, packaging material, binder or a vehicle for food products, feeds and pharmaceuticals. The film may be desirably colored, seasoned, or flavored.

(4) The film is fat-resistant. It is highly resistant to fat-soluble vitamins and fat-rich food products.

(5) The film is high in gas-barrier and flavor-locking abilities, but very low in oxygen-, air- and flavor-permeabilities. Either coating, packaging or sealing with the film stops the permeance of oxygen or air to effectively prevent the deterioration of food products, e.g. perishables, such as egg and fruit; fat-rich foods, such as dried fish, butter, cheese and chocolate; processed foods, such as ham and sausage; pharmaceuticals, such as vitamin, enzyme, hormone and antibiotics; seeds; and metals. The flavor-locking ability helps the film to prevent dispersion of the fragrances and/or aromas of fruit, tobacco and flavor.

(6) The film neither salts out nor loses its coating- and adhering-abilities when used for coating or packaging salts due to its high resistance to salts. It may be used to package or coat a salt, e.g. sodium chloride, potassium chloride, magnesium chloride, calcium chloride, etc; salt-rich food products, e.g. disjointed cod roe; laver; sesame; and/or a mixed seasoning, directed to "nigirimeshi (rice ball)" or "tsukemono (pickles)".

The gradually disintegrable molded article of the invention will be explained with reference to the following experiments using tablets.

EXPERIMENT 1

Preparation of mixtures containing pullulan and polysaccharide

Fifty-two and half grams of a mixture wherein pullulan and a polysaccharide were formulated as shown in Table 1 was dissolved in water by heating, filtered, concentrated in vacuo to about one-third in volume, and added with three volumes of methanol. The resultant sediment was recovered, dried in a stream of 40° C. air, and pulverized to obtain a powder mixture containing pullulan and the polysaccharide. The control powder was prepared similarly as above only with 52.5 g of pullulan.

TABLE I

Several mixtures of pullulan and polysaccharide

| No. | Formulation |
|-----|-------------|
| 1 | 50.0 g pullulan + 2.5 g gum arabic |
| 2 | 50.0 g pullulan + 2.5 g dextran |
| 3 | 50.0 g pullulan + 2.5 g elsinan |
| 4 | 50.0 g pullulan + 2.5 g guar gum |
| 5 | 50.0 g pullulan + 2.5 g carrageenan |
| 6 | 50.0 g pullulan + 2.5 g gum karaya |
| 7 | 50.0 g pullulan + 2.5 g konjak mannan |
| 8 | 50.0 g pullulan + 2.5 g locust bean gum |
| 9 | 50.0 g pullulan + 2.5 g pectin |
| 10 | 50.0 g pullulan + 2.5 g tara gum |
| 11 | 50.0 g pullulan + 2.5 g gum tragacanth |
| 12 | 50.0 g pullulan + 2.5 g xanthan gum |
| 13 | 52.5 g pullulan (control) |

EXPERIMENT 2

Preparation of tablets

Each powder, prepared in Experiment 1, was admixed with bromothymol blue (BTB) as an indicator for distintegration to give a BTB content of 5 mg/tablet, and directly prepared into tablets, 12 mm in diameter, 3 mm in thickness and about 0.45 g in weight, with a tableting machine.

EXPERIMENT 3

Disintegration test

The disintegration test on each tablet, prepared in Experiment 2, was carried out in accordance with the Japanese Pharmacopoeia: Three samples were placed in a disintegration tester, and subjected to a sucessive up- and down-motion, magnitude of 50 mm and frequency of 30 cycles/min, in 820 ml of 37° C. distilled water. In the course of the disintegration, the water was periodically sampled, and tested on the dissolution of the tablets. The BTB, released in the distilled water as the progress of the disintegration, was determined at the same time by measuring the absorbance of the water at 430 nm, and then the release ratio (%) to the total BTB release was calculated.

In each tablet, the release of BTB was almost linear up to 80% in terms of the release ratio. In relation to the dissolution/disintegration modes, the tested tablets were grouped as follows: Group I consisted of the tablets, containing pullulan along with either gum arabic, pectin, carrageenan or gum karaya, with a dissolution/disintegration rate higher than that of the control tablet; Group II, those, containing pullulan along with either dextran, elsinan, gum tragacanth or xanthan gum, with a dissolution/disintegration rate comparable to that of the control tablet; Group III, those, containing pullulan along with either guar gum or tara gum, with a dissolution/disintegration rate about 1.5 to 2.0-fold higher in terms of 80% release than that of the control tablet; and Group IV, those, containing pullulan along with either locust bean gum or konjak mannan, with a dissolution/disintegration rate about 2.0 to 3.0-fold higher in terms of 80% release than that of the control tablet.

The dissolution/disintegration modes as shown in FIG. 1 are typical of Groups I to IV. As is evident from these results, only the tablet containing pullulan along with heteromannan, i.e. galactomannan such as guar gum, tara gum and locust bean gum, and glucomannan such as konjak mannan, exhibits the gradual disintegration effect.

EXPERIMENT 4

Ratio of heteromannan to pullulan

The effect of the ratio of heteromannan to pullulan was studied with konjak mannan.

Fifty grams of pullulan powder was dissolved in the prescribed volume of 0.1 w/v % aqueous konjak mannan solution to give the formulation as shown in Table II, and treated similarly as in Experiment 1 to obtain a powder mixture. The control powder was prepared by dissolving 50 g of pullulan in 500 ml of water, and treating the resultant solution similarly as above.

TABLE II

| Konjak mannan solution (ml) | Konjak mannan (g) | Pullulan (g) | Ratio of heteromannan to pullulan (%) |
|---|---|---|---|
| 0 | 0 | 50 | 0 (control) |
| 500 | 0.5 | 50 | 1.0 |
| 1,250 | 1.25 | 50 | 2.5 |
| 2,500 | 2.5 | 50 | 5.0 |
| 5,000 | 5.0 | 50 | 10.0 |
| 10,000 | 10.0 | 50 | 20.0 |

Similarly as in Experiment 2, each powder was admixed with BTB, and tableted. The gradual disintegration effects of the resultant tablets were determined in the manner as described in Experiment 3 by periodically sampling the water, and comparing the time required for 80% release from each tablet with that from the control.

Figure 2:
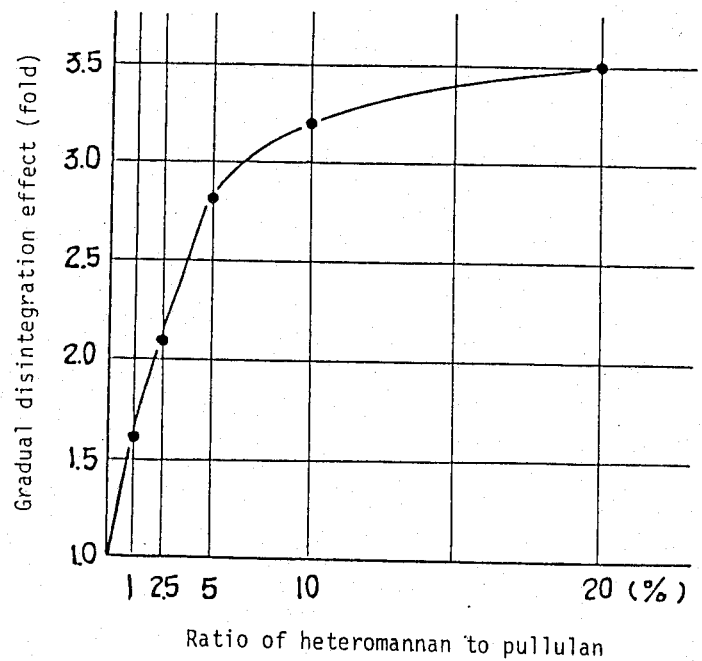
FIG. 2 graphically shows the relationship of the gradual disintegration effect of a tablet prepared from a powder mixture of pullulan and heteromannan versus the ratio of heteromannan to pullulan.

The results are given in FIG. 2.

As is evident from the results, the gradual disintegration effect drastically increases when the ratio of heteromannan to pullulan is increased from 1% to 10%, while the effect increases gradually when the ratio is increased to over 10%. We confirmed that a tablet with a heteromannan content exceeding the pullulan content had a tendency of causing deformation and/or cracking. Also was confirmed that powdered heteromannan per se did not provide a tablet because of its insufficient binding- and adhering-abilities.

As described above, the present invention facilitates the production of a molded article which gradually disintegrates and releases a drug by degrees under hydrous conditions to help to retain its efficacy for a prescribed time, and which has been deemed unrealizable. The molded article in accordance with the invention exhibits an improved resistance to sweat from the hand, dewdrop and to light wetting due to its decreased dissolution/disintegration rate under hydrous conditions. Thus, it is easily handleable and operable. The present invention overcomes the demerits of conventional molded articles with an excessive dissolution rate under hydrous conditions. Thus, it has expanded uses.

The invention will be more clearly understood by the following examples.

EXAMPLE 1

Film

A 15% aqueous pullulan solution, containing 10% guar gum and 0.1% sucrose monolaurate based on the pullulan solid, was casted on 60° C. chromium-plated roll, and taken off at a rate of 3 m/min to obtain a 0.03 mm-thick film which was then dried in a stream of 90° C. air.

The film is edible, and, unlike a film product prepared solely with pullulan, gradually dissolvable and disintegrable under hydrous conditions. Like a wafer, the film is advantageously usable for wrapping a bitter medicine powder. Since after dissolution and disintegration the film exhibits an appropriate adhesion, it can be used as a denture adhesive.

EXAMPLE 2

Sheet with seeds

A 12% aqueous pullulan solution, containing 20% locust bean gum and 0.1% sucrose monolaurate based on the pullulan solid, was mixed with 0.5 w/v % parsley seeds, continuously casted on an endless polyester belt to give thinnest possible layer, dried in a stream of 40° C. air, and continuously separated from the belt.

The sheet so obtained helps to retain the viability of the seeds over a long period of time. Since, unlike a sheet product prepared solely with pullulan, this sheet does not rapidly dissolve in sweat from handlers, the seeds can be sown in this form with ease. Since the sheet covering the seeds gradually dissolves and disintegrates in sprinkled water, the germination of the seeds is not prevented.

EXAMPLE 3

Capsule

A 15% aqueous pullulan solution, containing 20% guar gum and 1% maltitol based on the pullulan solid, was degassed by heating to 70° C. A 3 mm metal rod was then dipped in the solution, immediately pulled out, and gradually dried in a stream of 50° C. air to obtain a hard capsule.

Unlike a capsule product prepared solely with pullulan, this capsule is gradually dissolvable and disintegrable under hydrous conditions. The product is a high-quality, colorless and transparent capsule with a satisfiable gloss and an appropriate elasticity.

EXAMPLE 4

Tablet

Five parts of 2-(acetyloxy)benzoic acid was admixed with 6 parts of a mixture powder, prepared by the method in Experiment 1, and tableted with a 20 R pestle of 12 mm in diameter to produce tablets of 5.25 mm in thickness and 680 mg in weight.

The gradual release of 2-(acetyloxy)benzoic acid having efficacies of reducing fever and relieving aches results in the merits that the concentration in the digestive tract does not increase to an undesirable level, as well as that the efficacies are retained for several up to 10-odd hours. Since the tablet does not rapidly release the drug within the stomach, the possibilities of causing undesirable side effects including stomach disorder can be eliminated.

EXAMPLE 5

Tablet

Three parts of pullulan powder was admixed first with one part of locust bean gum powder, then with one part of a freeze-dried yoghurt powder and 0.2 parts of dried yeast powder. The resultant admixture was tableted by the method in Example 4.

The tablet helps to retain the viability of the yeast over a long period of time. The tablet gradually dissolves and disintegrates in the digestive tract to help to retain the intestine-regulating effect of the yeast and Lactobacillus microorganism over a long period of time.

EXAMPLE 6

Tablet

Five parts of pullulan powder was admixed first with one part of tara gum powder, then with two parts of zinc powder, after which the admixture was tableted by the method in Example 4.

The tablet gradually dissolves and disintegrates in a dilute sulfuric acid without causing a drastic reaction.

The tablet safely produces and supplies a constant level of hydrogen gas.

EXAMPLE 7

Fertilizer rod

Fourteen parts of a mixed fertilizer (N=14%, $P_2O_5$=8%, $K_2O$=12%), four parts of pullulan powder, one part of locust bean gum powder, one part of calcium sulfate and one part of water were admixed, and then subjected to 80° C. extruder, L/D=20, compression ratio=1.8, and die bore=30 mm, to produce a fertilizer rod.

This fertilizer rod is easily handleable, and does not necessarily require special packaging. The mechanical strength of the product is appropriate for deep placement, and the elution rate of the fertilizer elements can be regulated by employing different formulations.

While we have shown and described particular embodiments of our invention, it will be obvious to those skilled in the art that various changes and modifications may be made without departing from our invention in its broader aspects and we, therefore, intend in the appended claims to cover all such changes and modifications as fall within the true spirit and scope of our invention.

We claim:

1. In a molded article, the composition of which comprises pullulan, the improvement whereby the gradual disintegration properties of the article are improved, wherein the composition of the article consists essentially of a combination of pullulan and at least one heteromannan, the amount of heteromannan being, based on the dry solids, 1 to 100% of the pullulan.

2. The molded article in accordance with claim 1, wherein the heteromannan is a galactomannan.

3. The molded article in accordance with claim 1, wherein the heteromannan is a glucomannan.

4. The molded article in accordance with claim 1, wherein the heteromannan is a member selected from the group consisting of guar gum, tara gum, locust bean gum, konjak mannan, and mixtures thereof.

5. The molded article in accordance with claim 1, wherein the weight of the heteromannan solid is less than that of the pullulan solid.

6. The molded article in accordance with claim 1, which is a member selected from the group consisting of granule, fiber, filament, rod, gauze, cloth, film, sheet, paper, coating membrane, tube, capsule, tablet, and sponge.

7. The molded article in accordance with claim 5 wherein the heteromannan is, based on the dry solids basis, present in the range of 1–80% of the pullulan.

* * * * *